United States Patent
Bardy et al.

(10) Patent No.: US 8,718,760 B2
(45) Date of Patent: *May 6, 2014

(54) SUBCUTANEOUS IMPLANTABLE CARDIOVERTER-DEFIBRILLATOR PLACEMENT METHODS

(71) Applicant: Cameron Health, Inc., San Clemente, CA (US)

(72) Inventors: Gust H. Bardy, Seattle, WA (US); Riccardo Cappato, Ferrara (IT); Alan H. Ostroff, San Clemente, CA (US); William J. Rissmann, Coto de Caza, CA (US); Gary H. Sanders, Rancho Santa Margarita, CA (US)

(73) Assignee: Cameron Health Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/887,652

(22) Filed: May 6, 2013

(65) Prior Publication Data

US 2013/0261716 A1    Oct. 3, 2013

Related U.S. Application Data

(63) Continuation of application No. 11/680,107, filed on Feb. 28, 2007, now Pat. No. 8,447,398, which is a continuation of application No. 10/124,159, filed on Apr. 17, 2002, now Pat. No. 7,194,302, which is a continuation-in-part of application No. 09/940,283, filed on Aug. 27, 2001, now Pat. No. 7,065,407, and a continuation-in-part of application No. 09/940,371, filed on Aug. 27, 2001, now Pat. No. 7,039,465, and a continuation-in-part of application No. 09/940,468, (Continued)

(51) Int. Cl.
*A61N 1/00* (2006.01)

(52) U.S. Cl.
USPC ............................................................ 607/5

(58) Field of Classification Search
USPC ................................... 607/4, 5, 17, 119–123
See application file for complete search history.

(56) References Cited

U.S. PATENT DOCUMENTS

| 3,593,718 A | 7/1971 | Krasner |
| 3,713,449 A | 1/1973 | Mulier |

(Continued)

OTHER PUBLICATIONS

"U.S. Appl. No. 10/662,612, Advisory Action mailed May 10, 2007", 2 pgs.

(Continued)

*Primary Examiner* — Rex R Holmes
(74) *Attorney, Agent, or Firm* — Schwegman, Lundberg & Woessner, P.A.

(57) ABSTRACT

A subcutaneous cardiac device includes two electrodes and a stimulator that generates a pulse to the electrodes. The electrodes are implanted between the skin and the rib cage of the patient and are adapted to generate an electric field corresponding to the pulse, the electric field having a substantially uniform voltage gradient as it passes through the heart. The shapes, sizes, positions and structures of the electrodes are selected to optimize the voltage gradient of the electric field, and to minimize the energy dissipated by the electric field outside the heart. More specifically, the electrodes have contact surfaces that contact the patient tissues, said contact surfaces having a total contact area of less than 100 cm². In one embodiment, one or both electrodes are physically separated from the stimulator. In another embodiment, a unitary housing holds the both electrodes and the stimulator. Sensor circuitry may also include in the stimulator for detecting intrinsic cardiac activity through the same electrodes.

16 Claims, 12 Drawing Sheets

Related U.S. Application Data filed on Aug. 27, 2001, now abandoned, and a continuation-in-part of application No. 09/941,814, filed on Aug. 27, 2001, now abandoned, and a continuation-in-part of application No. 09/940,356, filed on Aug. 27, 2001, now abandoned, and a continuation-in-part of application No. 09/940,340, filed on Aug. 27, 2001, now Pat. No. 6,937,907, and a continuation-in-part of application No. 09/940,287, filed on Aug. 27, 2001, now abandoned, and a continuation-in-part of application No. 09/940,377, filed on Aug. 27, 2001, now Pat. No. 6,866,044, and a continuation-in-part of application No. 09/940,599,filed on Aug. 27, 2001, now Pat. No. 6,950,705, and a continuation-in-part of application No. 09/940,373, filed on Aug. 27, 2001, now Pat. No. 6,788,974, and a continuation-in-part of application No. 09/940,273, filed on Aug. 27, 2001, now Pat. No. 7,069,080, and a continuation-in-part of application No. 10/011,566, filed on Nov. 5, 2001, now Pat. No. 6,988,003, and a continuation-in-part of application No. 10/011,956, filed on Nov. 5, 2001, now Pat. No. 7,120,495, and a continuation-in-part of application No. 09/940,266, filed on Aug. 27, 2001, now Pat. No. 6,856,835, and a continuation-in-part of application No. 09/940,378, filed on Aug. 27, 2001, now Pat. No. 7,146,212, and a continuation-in-part of application No. 09/940,471, filed on Aug. 27, 2001, now Pat. No. 7,076,296, and a continuation-in-part of application No. 10/011,949, filed on Nov. 5, 2001, now Pat. No. 7,090,682, and a continuation-in-part of application No. 10/011,527, filed on Nov. 5, 2001, now Pat. No. 6,834,204, and a continuation-in-part of application No. 10/011,952, filed on Nov. 5, 2001, now Pat. No. 6,778,860, and a continuation-in-part of application No. 10/011,860, filed on Nov. 5, 2001, now Pat. No. 7,092,754, and a continuation-in-part of application No. 10/011,958, filed on Nov. 5, 2001, now abandoned, and a continuation-in-part of application No. 10/011,506, filed on Nov. 5, 2001, now abandoned, and a continuation-in-part of application No. 10/015,202, filed on Nov. 5, 2001, now Pat. No. 6,952,610, and a continuation-in-part of application No. 10/011,955, filed on Nov. 5, 2001, now Pat. No. 6,952,608, and a continuation-in-part of application No. 10/011,957, filed on Nov. 5, 2001, now Pat. No. 6,954,670, and a continuation-in-part of application No. 10/011,946, filed on Nov. 5, 2001, now Pat. No. 6,865,417, and a continuation-in-part of application No. 10/011,948, filed on Nov. 5, 2001, now Pat. No. 6,927,721, and a continuation-in-part of application No. 10/011,565, filed on Nov. 5, 2001, now abandoned, and a continuation-in-part of application No. 10/011,941, filed on Nov. 5, 2001, now Pat. No. 7,043,299, and a continuation-in-part of application No. 10/011,607, filed on Nov. 5, 2001, now Pat. No. 7,194,309, and a continuation-in-part of application No. 10/011,947, filed on Nov. 5, 2001, now Pat. No. 7,039,459, and a continuation-in-part of application No. 10/013,980, filed on Nov. 5, 2001, now Pat. No. 7,065,410, and a continuation-in-part of application No. 10/011,533, filed on Nov. 5, 2001, now abandoned, and a continuation-in-part of application No. 09/990,510, filed on Nov. 21, 2001, now Pat. No. 6,754,528.

(56) References Cited

U.S. PATENT DOCUMENTS

| | | |
|---|---|---|
| 3,807,411 A | 4/1974 | Harris et al. |
| 3,986,496 A | 10/1976 | Brastad |
| 3,987,799 A | 10/1976 | Purdy et al. |
| 4,094,321 A | 6/1978 | Muto |
| 4,290,430 A | 9/1981 | Bihn et al. |
| 4,349,030 A | 9/1982 | Belgard et al. |
| 4,406,286 A | 9/1983 | Stein |
| 4,412,541 A | 11/1983 | Schaldach et al. |
| 4,498,478 A | 2/1985 | Bourgeois |
| 4,543,956 A | 10/1985 | Herscovici |
| 4,702,253 A | 10/1987 | Nappholz et al. |
| 4,719,920 A | 1/1988 | Alt et al. |
| 4,825,871 A | 5/1989 | Cansell |
| 4,830,006 A | 5/1989 | Haluska et al. |
| 4,865,037 A | 9/1989 | Chin et al. |
| 4,878,497 A | 11/1989 | Callaghan et al. |
| 4,940,054 A | 7/1990 | Grevis et al. |
| 5,018,522 A | 5/1991 | Mehra |
| 5,083,562 A | 1/1992 | De Coriolis et al. |
| 5,179,946 A | 1/1993 | Weiss |
| 5,193,535 A | 3/1993 | Bardy et al. |
| 5,243,977 A | 9/1993 | Trabucco et al. |
| 5,243,978 A | 9/1993 | Duffin, Jr. |
| 5,261,401 A | 11/1993 | Baker et al. |
| 5,265,623 A | 11/1993 | Kroll et al. |
| 5,292,338 A | 3/1994 | Bardy |
| 5,318,591 A | 6/1994 | Causey, III et al. |
| 5,342,400 A | 8/1994 | Hirschberg et al. |
| 5,344,430 A | 9/1994 | Berg et al. |
| 5,358,514 A | 10/1994 | Schulman et al. |
| 5,360,442 A | 11/1994 | Dahl et al. |
| 5,366,485 A | 11/1994 | Kroll et al. |
| 5,388,578 A | 2/1995 | Yomtov et al. |
| 5,391,191 A | 2/1995 | Holmstrom |
| 5,411,537 A | 5/1995 | Munshi et al. |
| 5,441,518 A | 8/1995 | Adams et al. |
| 5,489,293 A | 2/1996 | Pless et al. |
| 5,507,785 A | 4/1996 | Deno |
| 5,514,160 A | 5/1996 | Kroll et al. |
| 5,522,853 A | 6/1996 | Kroll |
| 5,641,326 A | 6/1997 | Adams |
| 5,643,323 A | 7/1997 | Kroll et al. |
| 5,662,696 A | 9/1997 | Kroll et al. |
| 5,709,709 A | 1/1998 | Kroll |
| 5,772,690 A | 6/1998 | Kroll |
| 5,800,464 A | 9/1998 | Kieval |
| 5,800,470 A | 9/1998 | Stein et al. |
| 5,849,031 A | 12/1998 | Martinez et al. |
| 5,871,508 A | 2/1999 | Thompson et al. |
| 5,916,238 A | 6/1999 | Hauser et al. |
| 5,928,270 A | 7/1999 | Ramsey, III et al. |
| 5,964,787 A | 10/1999 | Kerver et al. |
| 5,968,079 A | 10/1999 | Warman et al. |
| 5,978,703 A | 11/1999 | Kroll et al. |
| 5,978,705 A | 11/1999 | KenKnight et al. |
| 5,987,352 A | 11/1999 | Klein et al. |
| 6,006,133 A | 12/1999 | Lessar et al. |
| 6,091,989 A | 7/2000 | Swerdlow et al. |
| 6,176,879 B1 | 1/2001 | Reischl |
| 6,187,028 B1 | 2/2001 | Munshi |
| 6,269,266 B1 | 7/2001 | Leysieffer |
| 6,283,985 B1 | 9/2001 | Harguth et al. |
| 6,519,493 B1 | 2/2003 | Florio et al. |
| 6,522,915 B1 | 2/2003 | Ceballos et al. |
| 6,539,257 B1 | 3/2003 | KenKnight |
| 6,757,311 B2 | 6/2004 | Abe et al. |
| 6,950,105 B2 | 9/2005 | Giemborek et al. |
| 7,062,329 B2 | 6/2006 | Ostroff et al. |
| 7,103,415 B2 | 9/2006 | Probst et al. |
| 7,149,575 B2 | 12/2006 | Ostroff et al. |
| 7,181,274 B2 | 2/2007 | Rissmann et al. |
| 7,289,854 B2 | 10/2007 | Bardy et al. |
| 7,349,736 B2 | 3/2008 | Ostroff et al. |
| 7,463,924 B2 | 12/2008 | Bardy et al. |
| 7,502,645 B2 | 3/2009 | Ostroff et al. |

(56) References Cited

U.S. PATENT DOCUMENTS

| | | | |
|---|---|---|---|
| 7,536,222 | B2 | 5/2009 | Bardy et al. |
| 7,570,997 | B2 | 8/2009 | Lovett et al. |
| 7,627,367 | B2 | 12/2009 | Warren et al. |
| 7,627,375 | B2 | 12/2009 | Bardy et al. |
| 7,657,311 | B2 | 2/2010 | Bardy et al. |
| 7,720,534 | B2 | 5/2010 | Bardy et al. |
| 7,720,536 | B2 | 5/2010 | Rissmann et al. |
| 7,751,885 | B2 | 7/2010 | Bardy et al. |
| 7,865,233 | B2 | 1/2011 | Haefner |
| 8,014,862 | B2 | 9/2011 | Ostroff et al. |
| 8,090,438 | B2 | 1/2012 | Bardy et al. |
| 8,135,459 | B2 | 3/2012 | Bardy et al. |
| 8,145,305 | B2 | 3/2012 | Ostroff et al. |
| 8,160,699 | B2 | 4/2012 | Bardy et al. |
| 8,386,037 | B2 | 2/2013 | Ostroff et al. |
| 8,412,320 | B2 | 4/2013 | Ostroff et al. |
| 8,577,454 | B2 | 11/2013 | Bardy et al. |
| 2002/0082658 | A1 | 6/2002 | Heinrich et al. |
| 2002/0147475 | A1 | 10/2002 | Scheiner et al. |
| 2003/0017372 | A1 | 1/2003 | Probst et al. |
| 2004/0220641 | A1 | 11/2004 | Wagner et al. |
| 2005/0277990 | A1 | 12/2005 | Ostroff et al. |
| 2008/0269813 | A1 | 10/2008 | Greenhut et al. |
| 2008/0319503 | A1 | 12/2008 | Honeck et al. |

OTHER PUBLICATIONS

"U.S. Appl. No. 10/662,612, Final Office Action mailed Mar. 8, 2007", 10 pgs.
"U.S. Appl. No. 10/662,612, Non Final Office Action mailed Sep. 12, 2006", 12 pgs.
"U.S. Appl. No. 10/662,612, Response filed May 2, 2007 to Final Office Action mailed Mar. 8, 2007", 10 pgs.
"U.S. Appl. No. 10/662,612, Response filed Dec. 5, 2006 to Non Final Office Action mailed Sep. 12, 2006", 13 pgs.
"U.S. Appl. No. 10/790,903, Final Office Action mailed Dec. 27, 2005", 8 pgs.
"U.S. Appl. No. 10/790,903, Non Final Office Action mailed Jul. 12, 2005", 9 pgs.
"U.S. Appl. No. 10/790,903, Response filed Feb. 17, 2006 to Final Office Action mailed Dec. 27, 2005", 6 pgs.
"U.S. Appl. No. 10/790,903, Response filed Oct. 11, 2005 to Non Final Office Action mailed Jul. 12, 2005", 15 pgs.
"U.S. Appl. No. 10/984,392, Non Final Office Action mailed May 16, 2006", 9 pgs.
"U.S. Appl. No. 10/984,392, Response filed Aug. 1, 2006 to Non Final Office Action mailed May 16, 2006", 8 pgs.
"U.S. Appl. No. 10/984,585, Non Final Office Action mailed Mar. 14, 2007", 15 pgs.
"U.S. Appl. No. 10/984,585, Non Final Office Action mailed May 30, 2008", 10 pgs.
"U.S. Appl. No. 10/984,585, Non Final Office Action mailed Nov. 19, 2007", 9 pgs.
"U.S. Appl. No. 10/984,585, Response filed Feb. 18, 2008 to Non Final Office Action mailed Nov. 19, 2007", 9 pgs.
"U.S. Appl. No. 10/984,585, Response filed Jun. 12, 2007 to Non Final Office Action mailed Mar. 14, 2007", 12 pgs.
"U.S. Appl. No. 10/984,585, Response filed Sep. 30, 2008 to Non Final Office Action mailed May 30, 2008", 7 pgs.
"U.S. Appl. No. 11/060,869, Final Office Action mailed Sep. 11, 2007", 7 pgs.
"U.S. Appl. No. 11/060,869, Non Final Office Action mailed Mar. 19, 2007", 13 pgs.
"U.S. Appl. No. 11/060,869, Non Final Office Action mailed May 23, 2008", 10 pgs.
"U.S. Appl. No. 11/060,869, Response filed Jun. 1, 2007 to Non Final Office Action mailed Mar. 19, 2007", 13 pgs.
"U.S. Appl. No. 11/060,869, Response filed Aug. 22, 2008 to Non Final Office Action mailed May 23, 2008", 11 pgs.
"U.S. Appl. No. 11/060,869, Response filed Oct. 30, 2007 to Final Office Action mailed Sep. 11, 2007", 8 pgs.

"U.S. Appl. No. 11/205,447, Advisory Action mailed Sep. 24, 2012", 3 pgs.
"U.S. Appl. No. 11/205,447, Final Office Action mailed Feb. 2, 2012", 6 pgs.
"U.S. Appl. No. 11/205,447, Final Office Action mailed Jul. 12, 2012", 9 pgs.
"U.S. Appl. No. 11/205,447, Non Final Office Action mailed Mar. 21, 2012", 8 pgs.
"U.S. Appl. No. 11/205,447, Non Final Office Action mailed Sep. 21, 2011", 7 pgs.
"U.S. Appl. No. 11/205,447, Response filed Feb. 29, 2012 to Final Office Action mailed Feb. 2, 2012", 5 pgs.
"U.S. Appl. No. 11/205,447, Response filed Jun. 19, 2012 to Non Final Office Action mailed Mar. 21, 2012", 10 pgs.
"U.S. Appl. No. 11/205,447, Response filed Sep. 12, 2012 to Final Office Action mailed Jul. 12, 2012", 15 pgs.
"U.S. Appl. No. 11/205,447, Response filed Nov. 12, 2012 to Advisory Action mailed Sep. 24, 2012", 16 pgs.
"U.S. Appl. No. 11/205,447, Response filed Dec. 15, 2011 to Non Final Office Action mailed Sep. 21, 2011", 6 pgs.
"U.S. Appl. No. 11/349,326, Advisory Action mailed Jan. 13, 2009", 4 pgs.
"U.S. Appl. No. 11/349,326, Final Office Action mailed Jan. 22, 2010", 8 pgs.
"U.S. Appl. No. 11/349,326, Final Office Action mailed Oct. 24, 2008", 12 pgs.
"U.S. Appl. No. 11/349,326, Non Final Office Action mailed May 5, 2009", 8 pgs.
"U.S. Appl. No. 11/349,326, Non Final Office Action mailed May 13, 2008", 13 pgs.
"U.S. Appl. No. 11/349,326, Response filed Feb. 24, 2009 to Advisory Action mailed Jan. 13, 2009", 4 pgs.
"U.S. Appl. No. 11/349,326, Response filed Apr. 22, 2010 to Final Office Action mailed Jan. 22, 2010", 6 pgs.
"U.S. Appl. No. 11/349,326, Response filed Aug. 5, 2009 to Non Final Office Action mailed May 5, 2009", 10 pgs.
"U.S. Appl. No. 11/349,326, Response filed Aug. 13, 2008 to Non Final Office Action mailed May 13, 2008", 7 pgs.
"U.S. Appl. No. 11/349,326, Response filed Dec. 24, 2008 to Final Office Action mailed Oct. 24, 2008", 8 pgs.
"U.S. Appl. No. 11/447,531, Advisory Action mailed Mar. 20, 2009", 3 pgs.
"U.S. Appl. No. 11/447,531, Final Office Action mailed Jan. 2, 2009", 8 pgs.
"U.S. Appl. No. 11/447,531, Non Final Office Action mailed Apr. 27, 2009", 5 pgs.
"U.S. Appl. No. 11/447,531, Non Final Office Action mailed Jul. 11, 2008", 11 pgs.
"U.S. Appl. No. 11/447,531, Response filed Mar. 2, 2009 to Final Office Action mailed Jan. 2, 2009", 9 pgs.
"U.S. Appl. No. 11/447,531, Response filed Mar. 12, 2008 to Restriction Requirement mailed Feb. 12, 2008", 7 pgs.
"U.S. Appl. No. 11/447,531, Response filed Apr. 2, 2009 to Advisory Action mailed Mar. 20, 2009", 10 pgs.
"U.S. Appl. No. 11/447,531, Response filed Jul. 24, 2009 to Non Final Office Action mailed Apr. 27, 2008", 3 pgs.
"U.S. Appl. No. 11/447,531, Response filed Oct. 10, 2008 to Non Final Office Action mailed Jul. 11, 2008", 13 pgs.
"U.S. Appl. No. 11/447,711, Final Office Action mailed Apr. 7, 2009", 11 pgs.
"U.S. Appl. No. 11/447,711, Final Office Action mailed Jun. 19, 2009", 7 pgs.
"U.S. Appl. No. 11/447,711, Non Final Office Action mailed Nov. 7, 2008", 10 pgs.
"U.S. Appl. No. 11/447,711, Response filed Feb. 6, 2009 to Non Final Office Action mailed Nov. 7, 2008", 10 pgs.
"U.S. Appl. No. 11/447,711, Response filed Jun. 8, 2009 to Final Office Action mailed Apr. 7, 2009", 9 pgs.
"U.S. Appl. No. 11/447,711, Response filed Aug. 3, 2009 to Final Office Action mailed Jun. 19, 2009", 3 pgs.
"U.S. Appl. No. 11/451,241, Non Final Office Action mailed Mar. 31, 2009", 7 pgs.

(56) References Cited

OTHER PUBLICATIONS

"U.S. Appl. No. 11/451,241, Response filed Apr. 15, 2009 to Non Final Office Action mailed Mar. 31, 2009", 11 pgs.
"U.S. Appl. No. 11/553,785, Final Office Action mailed Aug. 19, 2009", 11 pgs.
"U.S. Appl. No. 11/553,785, Non Final Office Action mailed Mar. 9, 2009", 7 pgs.
"U.S. Appl. No. 11/553,785, Response filed Jun. 9, 2009 to Non Final Office Action mailed Mar. 9, 2009", 10 pgs.
"U.S. Appl. No. 11/553,785, Response filed Nov. 19, 2009 to Final Office Action mailed Aug. 19, 2009", 12 pgs.
"U.S. Appl. No. 11/554,185, Final Office Action mailed Jun. 14, 2013", 11 pgs.
"U.S. Appl. No. 11/554,185, Final Office Action mailed Sep. 30, 2013", 8 pgs.
"U.S. Appl. No. 11/554,185, Final Office Action Mailed Sep. 30, 2013", 7 pgs.
"U.S. Appl. No. 11/554,185, Non Final Office Action mailed Dec. 3, 2012", 10 pgs.
"U.S. Appl. No. 11/554,185, Response filed Mar. 1, 2013 to Non Final Office Action mailed Dec. 3, 2012", 9 pgs.
"U.S. Appl. No. 11/554,185, Response filed Sep. 6, 2013 to Final Office Action mailed Jun. 14, 2013", 7 pgs.
"U.S. Appl. No. 11/555,424, Non Final Office Action mailed Apr. 6, 2009", 8 pgs.
"U.S. Appl. No. 11/555,447, Non Final Office Action mailed Apr. 8, 2009", 7 pgs.
"U.S. Appl. No. 11/555,459, Non Final Office Action mailed Apr. 9, 2009", 9 pgs.
"U.S. Appl. No. 11/679,634, Final Office Action mailed Dec. 16, 2009", 7 pgs.
"U.S. Appl. No. 11/679,634, Non Final Office Action mailed Jun. 10, 2009", 10 pgs.
"U.S. Appl. No. 11/679,634, Response filed Feb. 16, 2010 to Final Office Action mailed Dec. 16, 2009", 8 pgs.
"U.S. Appl. No. 11/679,634, Response filed Sep. 10, 2009 to Non Final Office Action mailed Jun. 10, 2009", 10 pgs.
"U.S. Appl. No. 12/781,668, 312 Amendment filed May 20, 2011", 6 pgs.
"U.S. Appl. No. 13/429,777, Examiner Interview Summary mailed Jun. 6, 2012", 1 pg.
"U.S. Appl. No. 13/429,777, Non Final Office Action mailed Jun. 6, 2012", 9 pgs.
"U.S. Appl. No. 13/429,777, Response filed Sep. 6, 2012 to Non Final Office Action mailed Jun. 6, 2012", 8 pgs.
"U.S. Appl. No. 13/436,417, Non Final Office Action mailed Aug. 23, 2013", 5 pgs.
"U.S. Appl. No. 13/436,417, Response filed Dec. 20, 2012 to Restriction Requirement mailed Nov. 28, 2012", 7 pgs.
"U.S. Appl. No. 13/476,940, Application filed May 21, 2012", 53 pgs.
"U.S. Appl. No. 13/476,940, Preliminary Amendment filed Jun. 20, 2012", 27 pgs.
"U.S. Appl. No. 13/785,894, Final Office Action mailed Sep. 16, 2013", 8 pgs.
"U.S. Appl. No. 13/785,894, Non Final Office Action mailed Apr. 30, 2013", 9 pgs.
"U.S. Appl. No. 13/785,894, Response filed Aug. 30, 2013 to Non Final Office Action mailed Apr. 30, 2013", 10 pgs.
"U.S. Appl. No. 60/272,962, filed Feb. 28, 2001", 6 pgs.
"European Application Serial No. 01973151.2, Office Action mailed Jan. 20, 2011", 5 pgs.
"European Application Serial No. 01973151.2, Office Action mailed Aug. 28, 2006", 4 pgs.
"European Application Serial No. 01973151.2, Response filed May 19, 2011 to Office Action mailed Jan. 20, 2011", 16 pgs.
"European Application Serial No. 01973151.2, Response filed Dec. 20, 2006 to Office Action mailed Aug. 28, 2006", 22 pgs.
"European Application Serial No. 019731512, Summons to Attend Oral Proceedings mailed Oct. 11, 2013", 6 pgs.
"European Application Serial No. 02777694.7, Decision to Grant patent mailed Mar. 7, 2013", 2 pgs.
"European Application Serial No. 02777694.7, Office Action mailed Jan. 9, 2013", 5 pgs.
"European Application Serial No. 02777694.7, Office Action mailed Jul. 31, 2009", 5 pgs.
"European Application Serial No. 02777694.7, Office Action mailed Aug. 13, 2012", 5 pgs.
"European Application Serial No. 02777694.7, Response filed Dec. 8, 2009 to Office Action mailed Jul. 31, 2009", 5 pgs.
"European Application Serial No. 02777694.7, Response filed Dec. 14, 2012 to Office Action mailed Aug. 13, 2012", 2 pgs.
"European Application Serial No. 02785702.8, Office Action mailed Jul. 31, 2009", 5 pgs.
"European Application Serial No. 02785702.8, Office Action mailed Aug. 8, 2012", 5 pgs.
"European Application Serial No. 02785702.8, Office Action mailed Dec. 7, 2012", 5 pgs.
"European Application Serial No. 02785702.8, Response filed Dec. 8, 2009 to Office Action mailed Jul. 31, 2009", 5 pgs.
"International Application Serial No. PCT/IB2002/003481, International Preliminary Examination Report mailed Sep. 2, 2003", 5 pgs.
"International Application Serial No. PCT/IB2002/003502, International Preliminary Examination Report mailed Sep. 2, 2003", 5 pgs.
"International Application Serial No. PCT/IB2002/003502, International Search Report mailed Feb. 20, 2003", 4 pgs.
"International Application Serial No. PCT/IB2002/003469, Written Opinion mailed May 12, 2003", 5 pgs.
"International Application Serial No. PCT/IB2002/003484, International Search Report mailed Feb. 14, 2003", 5 pgs.
"International Application Serial No. PCT/IB2002/003484, Written Opinion mailed May 12, 2003", 5 pgs.
"International Application Serial No. PCT/IB2002/003503, International Preliminary Examination Report mailed Sep. 2, 2003", 5 pgs.
"International Application Serial No. PCT/IB2002/003503, International Search Report mailed Feb. 18, 2003", 4 pgs.
"International Application Serial No. PCT/IB2002/003503, Written Opinion mailed May 12, 2003", 5 pgs.
"International Application Serial No. PCT/IB2002/003522, International Preliminary Examination Report mailed Sep. 2, 2003", 5 pgs.
"International Application Serial No. PCT/IB2002/003522, International Search Report mailed Feb. 14, 2003", 4 pgs.
"International Application Serial No. PCT/IB2002/003522, Written Opinion mailed May 12, 2003", 6 pgs.
"International Application Serial No. PCT/IB2002/004490, International Search Report mailed Apr. 16, 2003", 3 pgs.
"International Application Serial No. PCT/IB2002/004498, International Search Report mailed Apr. 16, 2003", 8 pgs.
"International Application Serial No. PCT/IB2002/004507, International Search Report mailed Apr. 16, 2003", 4 pgs.
"International Application Serial No. PCT/IB2002/003469, International Preliminary Examination Report mailed Sep. 2, 2003", 5 pgs.
"International Application Serial No. PCT/IB2002/003469, International Search Report mailed Feb. 14, 2003", 4 pgs.
"International Application Serial No. PCT/US2001/029106, International Preliminary Examination Report mailed Dec. 18, 2002", 6 pgs.
"International Application Serial No. PCT/US2001/029106, International Search Report mailed Mar. 21, 2002", 4 pgs.
"International Application Serial No. PCT/US2001/029106, Written Opinion mailed Sep. 3, 2002".
"International Application Serial No. PCT/US2001/029168, International Preliminary Examination Report mailed Nov. 20, 2002", 7 pgs.
"International Application Serial No. PCT/US2001/029168, International Search Report mailed Mar. 26, 2002", 5 pgs.
"International Application Serial No. PCT/US2001/029168, Written Opinion mailed Sep. 10, 2002", 7 pgs.
"International Application Serial No. PCT/US2003/010666, International Search Report mailed Oct. 1, 2003", 1 pg.
Bardy, Gust H, et al., "U.S. Appl. No. 09/663,606, filed Sep. 18, 2000", 32 pgs.
Bardy, Gust H, et al., "U.S. Appl. No. 09/663,607, filed Sep. 18, 2000", 41 pgs.

SUBCUTANEOUS IMPLANTABLE CARDIOVERTER-DEFIBRILLATOR PLACEMENT METHODS

RELATED APPLICATIONS

This application is a continuation of U.S. patent application Ser. No. 11/680,107, filed Feb. 28, 2007, and now U.S. Pat. No. 8,447,398, which is a continuation of U.S. patent application Ser. No. 10/124,159, filed Apr. 17, 2002, and now U.S. Pat. No. 7,194,302, the entire disclosures of each of which are incorporated herein by reference; which is a continuation-in-part application to the following applications, the disclosures of which are all incorporated herein by reference: U.S. application Ser. No. 09/940,283, filed Aug. 27, 2001, now U.S. Pat. No. 7,065,407; U.S. application Ser. No. 09/940,371, filed Aug. 27, 2001, now U.S. Pat. No. 7,039,465; U.S. application Ser. No. 09/940,468, filed Aug. 27, 2001, published as U.S. 2002-0035379 A1, and now abandoned; U.S. application Ser. No. 09/941,814, filed Aug. 27, 2001, published as U.S. 2002-0035381 A1, and now abandoned; U.S. application Ser. No. 09/940,356, filed Aug. 27, 2001, published as U.S. 2002-0035378 A1, and now abandoned; U.S. application Ser. No. 09/940,340, filed Aug. 27, 2001, now U.S. Pat. No. 6,937,907; U.S. application Ser. No. 09/940,287, filed Aug. 27, 2001, published as U.S. 2002-0035377 A1, and now abandoned; U.S. application Ser. No. 09/940,377, filed Aug. 27, 2001, now U.S. Pat. No. 6,866,044; U.S. application Ser. No. 09/940,599, filed Aug. 27, 2001, now U.S. Pat. No. 6,950,705; U.S. application Ser. No. 09/940,373, filed Aug. 27, 2001, now U.S. Pat. No. 6,788,974; U.S. application Ser. No. 09/940,273, filed Aug. 27, 2001, now U.S. Pat. No. 7,069,080; U.S. application Ser. No. 10/011,566, filed Nov. 5, 2001, now U.S. Pat. No. 6,988,003; U.S. application Ser. No. 10/011,956, filed Nov. 5, 2001, now U.S. Pat. No. 7,120,495; U.S. application Ser. No. 09/940,266, filed Aug. 27, 2001, now U.S. Pat. No. 6,856,835; U.S. application Ser. No. 09/940,378, filed Aug. 27, 2001, now U.S. Pat. No. 7,146,212; U.S. application Ser. No. 09/940,471, filed Aug. 27, 2001, now U.S. Pat. No. 7,076,296; U.S. application Ser. No. 10/011,949, filed Nov. 5, 2001, now U.S. Pat. No. 7,090,682; U.S. application Ser. No. 10/011,527, filed Nov. 5, 2001, now U.S. Pat. No. 6,834,204; U.S. application Ser. No. 10/011,952, filed Nov. 5, 2001, now U.S. Pat. No. 6,778,860; U.S. application Ser. No. 10/011,860, filed Nov. 5, 2001, now U.S. Pat. No. 7,092,754; U.S. application Ser. No. 10/011,958, filed Nov. 5, 2001, published as U.S. 2002-0095184 A1, and now abandoned; U.S. application Ser. No. 10/011,506, filed Nov. 5, 2001, published as U.S. 2002-0107544 A1, and now abandoned; U.S. application Ser. No. 10/015,202, filed Nov. 5, 2001, now U.S. Pat. No. 6,952,610; U.S. application Ser. No. 10/011,955, filed Nov. 5, 2001, now U.S. Pat. No. 6,952,608; U.S. application Ser. No. 10/011,957, filed Nov. 5, 2001, now U.S. Pat. No. 6,954,670; U.S. application Ser. No. 10/011,946, filed Nov. 5, 2001, now U.S. Pat. No. 6,865,417; U.S. application Ser. No. 10/011,948, filed Nov. 5, 2001, now U.S. Pat. No. 6,927,721; U.S. application Ser. No. 10/011,565, filed Nov. 5, 2001, published as U.S. 2003-0088277 A1, and now abandoned; U.S. application Ser. No. 10/011,941, filed Nov. 5, 2001, now U.S. Pat. No. 7,043,299; U.S. application Ser. No. 10/011,607, filed Nov. 5, 2001 and now U.S. Pat. No. 7,194,309; U.S. application Ser. No. 10/011,947, filed Nov. 5, 2001, now U.S. Pat. No. 7,039,459; U.S. application Ser. No. 10/013,980, filed Nov. 5, 2001, now U.S. Pat. No. 7,065,410; U.S. application Ser. No. 10/011,533, filed Nov. 5, 2001, published as U.S. 2002-0107545 A1, and now abandoned; and U.S. application Ser. No. 09/990,510, filed Nov. 21, 2001, now U.S. Pat. No. 6,754,528.

FIELD OF THE INVENTION

The present invention relates to a device and method for performing electrical cardiac stimulation, including cardioversion, defibrillation and, optionally, pacing of the heart using subcutaneous electrodes. The positions of the electrodes are optimized so that they can be used to generate an effective electric field across the heart with the electrodes having a small contact surface.

BACKGROUND OF THE INVENTION

The heart is a mechanical pump that is stimulated by electrical impulses. The mechanical action of the heart results in the flow of blood. During a normal heartbeat, the right atrium (RA) fills with blood from the returning veins. The RA then contracts and this blood is moved into the right ventricle (RV). When the RV contracts it pumps the blood to the lungs. Blood returning from the lungs moves into the left atrium (LA) and, after LA contraction, is pumped into the left ventricle (LV), which then pumps it throughout the body. Four heart valves keep the blood flowing in the proper directions.

The electrical signal that drives the mechanical contraction starts in the sin θ-atrial node, a collection of specialized heart cells in the right atrium that automatically depolarize (change their potential). The depolarization wavefront passes across all the cells of both atria and results in atrial contractions. When the advancing wavefront reaches the A-V node, it is delayed so that the contracting atria have time to fill the ventricles. The depolarizing wavefront then passes across the ventricles, causing them to contract and to pump blood to the lungs and body. This electrical activity occurs approximately 72 times a minute in a normal individual and is called normal sinus rhythm.

Abnormal electrical conditions can occur that can cause the heart to beat irregularly; these irregular beats are known as cardiac arrhythmias. Cardiac arrhythmias fall into two broad categories: slow heart beats or bradyarrhythmia and fast heart beats or tachyarrhythmia, clinically referred to as bradycardia and tachycardia, respectively. Bradycardia often results from abnormal performance of the AV node. Stimuli generated by the heart's own natural pacemaker, the SA node, are improperly conducted to the rest of the heart's conduction system; as a result, other stimuli are generated although their intrinsic rate is below the SA node's intrinsic rate. Clinical symptoms associated with bradycardia include lack of energy, dizziness, etc., as the heart beats more slowly than is usual.

Bradycardia has been treated for years with implantable pacemakers. Their primary function is to monitor the heart's intrinsic rhythm and to generate a stimulus strong enough to initiate a cardiac contraction in the absence of the heart's own intrinsic beat. Typically, these pacemakers operate in a demand mode in which the stimulus is applied if the intrinsic rhythm is below a predetermined threshold.

Tachycardia is often associated with cardiac fibrillation, a condition in which the electrically coordinated aspects of the cardiac wave fronts are lost and, instead, have degenerated into chaotic, almost random electrical stimulations of the heart. Tachycardia often results from ischemic heart disease in which local myocardium performance is compromised As a result of tachycardia, coordinated contraction of heart tissue is lost which leads to a loss of blood flow to the rest of the body. Brain death can occur within several minutes of tachycardia, followed by complete death several minutes later if the tachycardia is left untreated.

Application of an electrical stimulus to a critical mass of cardiac tissue can be effective in extending the refractory aspects such that the heart can recover from its chaotic condition and resume normal coordinated propagation of electrical stimulation wave fronts that result in the resumption of normal blood flow. Thus, the application of an electrical stimulus can revert a patient's heart to a sinus cardiac rhythm and the chambers of the heart once again act to pump in a coordinated fashion. Such a stimulus is known as defibrillation.

Cardioversion/defibrillation is a technique employed to counter arrhythmic heart conditions including some tachycardias in the atria and/or ventricles. Typically, electrodes are employed to stimulate the heart with high energy electrical impulses or shocks, of a magnitude substantially greater than the intrinsic cardiac signals. The purpose of these high energy signals is to disrupt the generation of the chaotic cardiac signals and cause the heart to revert to a sinus rhythm.

There are two kinds of conventional cardioversion/defibrillation systems: internal cardioversion/defibrillation devices, or ICDs, and external automatic defibrillators, or AEDs. An ICD includes a housing containing a pulse generator, electrodes and leads connecting the electrodes to the housing. The electrodes are implanted transvenously in the cardiac chambers or are attached to the external walls of the heart. Various structures of these types are disclosed in U.S. Pat. Nos. 4,603,705; 4,693,253; 4,944,300; 5,105,810; 4,567,900; and 5,618,287, all of which are incorporated herein by reference.

In addition, U.S. Pat. Nos. 5,342,407 and 5,603,732, incorporated herein by reference, disclose an ICD with a pulse generator implanted in the abdomen and two electrodes. In one embodiment (FIG. 22), the two electrodes 188, 190 are implanted subcutaneously and disposed in the thoracic region, outside of the ribs and on opposite sides of the heart. In another embodiment (FIG. 23), one electrode 206 is attached to the epicardial tissues and another electrode 200 is disposed inside the rib cage. In a third embodiment (FIG. 24), one electrode 208 is disposed away from the heart and the other electrode 210 is disposed inside the right ventricle. This system is very complicated and it is difficult to implant surgically since it requires three separate incisions.

Recently, some ICDs have been made with an electrode on the housing of the pulse generator, as illustrated in U.S. Pat. Nos. 5,133,353; 5,261,400; 5,620,477; and 5,658,325; all of which are incorporated herein by reference.

ICDs have proven to be very effective for treating various cardiac arrhythmias and are now an established therapy for the management of life threatening cardiac rhythms, such as ventricular fibrillation. However, commercially available ICDs have several disadvantages. First, they must be implanted using somewhat complex and expensive surgical procedures that are performed by specially trained physicians. Second, they rely on transvenous leads for the placement of at least one electrode within the cardiac chambers. It has been found that over a period of time the electrodes get dislodged from the cardiac tissues, undesirable tissue formations may deposit on the electrodes, or the leads can break. These problems are especially acute when leads carry two or more electrodes. Third, removing these ICDs and replacing them, if necessary, also requires complicated surgical procedures that may be more life-threatening than the initial implantation.

As mentioned above, AEDs are also employed to provide antiarrhythmic therapy. A typical AED is similar to an ICD in that it also includes a pulse generator and a pair of electrodes connected to the pulse generator by leads. Because all of these elements are external, they can be made larger than the corresponding elements of an ICD. Moreover, because the electrodes are applied externally, an AED typically requires more power than an ICD.

Three types of AEDs are presently available. One type is normally used in a hospital or similar facility and is designed to be used by a trained physician when a patient is suffering from an acute tachyarrhythmia.

The second type is placed in public places such as theaters, airports, and so on, and is designed to be used in an emergency by people with less training, such as medical technicians, or even lay persons. Both the first and second types of AED require some kind of intervention by a person before operation.

A third type of AED has been proposed which is adapted to be worn by a patient, and which could function without an operator.

All three types of AEDs require the application of external electrodes which are uncomfortable. Even the third type of AED presents at best only a short term solution to cardiac arrhythmia.

OBJECTIVES AND SUMMARY OF THE INVENTION

An objective of the present invention is to provide a subcutaneous cardiac stimulator device having electrodes with small areas, yet capable of generating a relative and effective electric field through the heart of a patient.

A further objective is to provide a subcutaneous cardiac stimulator device that has been optimized by adjusting several design parameters that control and affect the size, shape and structure of the device.

Yet another objective is to provide a subcutaneous cardiac stimulator device that does not include any leads extending into or touching a patient's heart.

Briefly, a subcutaneous device is provided with at least two electrodes and a stimulator for generating pulses applied to the electrodes. In one embodiment, the two electrodes are generally flat and are adapted to be implanted at predetermined positions outside the patient's rib cage. More specifically, one electrode is adapted to be implanted near the sternum and the second electrode is adapted to be implanted on the left side of the patient. When a pulse is applied between the electrodes an electric field is generated. The positions of the electrodes are chosen so that the electric field is effective for defibrillation. The electrode sizes, including their contact surfaces, shapes and structures are optimized as well to reduce the energy dissipated outside the heart during each pulse. More specifically, the total contact surface area of the two electrodes is less than 100 cm$^2$.

In another embodiment, a unitary device is provided with a housing containing a cardiac stimulator adapted to generate electrical pulses and two electrodes formed on the housing and coupled to the cardiac stimulator within the housing. The unitary device is implanted subcutaneously between the skin and the rib cage of the patient. Preferably, the unitary device is positioned between two of the ribs, and is oriented so that its electrodes generate an electric field that has a voltage gradient as it passes through the heart that is sufficient to defibrillate the heart.

In accordance with this invention, a cardiac device is provided which includes first and second subcutaneous electrodes and a cardiac stimulator electrically connected to the first and second electrodes and adapted to apply electrical pulses between the first and second electrodes. The first and second electrodes cooperate with the cardiac stimulator to generate an electric field characterized by a substantially constant voltage gradient across a substantial portion of the heart of a patient when the first and second electrodes are implanted at respective first and second positions within the patient. The electrodes are sized and shaped so that their total contact surface (the surface that contacts the patient's tissues) is less than 100 cm$^2$.

Another aspect of the invention concerns a cardiac device with an anterior and a posterior electrode, each electrode having an inner and an outer surface, and a cardiac stimulator electrically connected to the electrodes and adapted to selectively apply electrical pulses between the electrodes. The electrodes are adapted to be implanted subcutaneously with the inner surfaces being in contact with the body tissues and pointing inwardly toward the heart, the inner surfaces being metallic surfaces that present a low tissue/electrode interface when implanted. Preferably, the anterior electrode is disposed adjacent to the sternum, and its inner surface area is no greater than the inner surface area of the posterior electrode. In one embodiment, the surface area of the anterior electrode is less than 20 cm$^2$ and preferably in the range of 5-15 cm$^2$ and the surface area of the posterior electrode is less than 50 cm$^2$ and preferably in the range of 15-40 cm$^2$.

The voltage on the electrodes is selected so that the electric field has a sufficient intensity to defibrillate the heart. Preferably the electric field has a voltage gradient in the range of about 3-8 V/cm across the cardiac tissues.

Another aspect of the invention concerns a cardiac device having two electrodes and a cardiac stimulator electrically connected to and selectively generating electrical pulses between the electrodes. One of the electrodes is implanted subcutaneously in the vicinity of the sternum with its geometric center being disposed on a first line perpendicular to the central axis through the patient. The second electrode is adapted to be implanted subcutaneously on the left side of the patient with its center being disposed on a second line perpendicular to the central axis. The first and second lines define a predetermined angle therebetween. Preferably, the first line defines an angle of 5 to 30 degrees with a third line extending perpendicularly from the central axis and extending from the central axis to the sternum. Preferably, the second line defines an angle of 60-120 degrees with the third line. Preferably, the first and second lines define an angle less than 90 degrees.

The geometric centers of the electrodes are separated from each other by a chord length of 15-25 cm.

Another aspect of the invention concerns a cardiac device including a first electrode and a second electrode, and a cardiac stimulator electrically connected to the electrodes and adapted to selectively apply electrical pulses between the electrodes. The electrodes are adapted to be implanted subcutaneously, with the first electrode being positioned adjacent to the sternum and the second electrode being adapted to be implanted subcutaneously at a distance of 15-35 cm from the first electrode, the distance being measured along an imaginary line extending circumferentially around the patient from the sternum at a distance of about 0-3 cm from the ribs. The first and second electrodes are adapted to be implanted in the same plane perpendicular to the patient's central axis. The electrodes are adapted to be implanted to generate an electric field in a plane that endeavors to pass through the center of the heart.

In one embodiment, the outer surface of either or both electrodes is also a conductive surface so that when the respective electrode is implanted, the outer surface is in electrical contact with the body tissues as well, thereby reducing the electrode interface resistance. In an alternate embodiment, the outer surface of one or both electrodes can be coated with a non-conductive material.

Preferably, the electrodes are formed with rounded edges and without sharp corners to insure that the electric field between the electrodes is not concentrated at these edges.

Another aspect of the invention concerns a unitary cardiac device formed of two subcutaneous electrodes both mounted on a rigid housing; and a cardiac stimulator within the housing electrically connected to the two electrodes and adapted to apply electrical pulses between the first and second electrodes. The two electrodes cooperate with the cardiac stimulator to generate an electric field characterized by substantially parallel field lines across a substantial portion of the heart of a patient when the housing is implanted in a plane that is perpendicular to the patient's central axis and passes through the patient's sternum.

The cardiac stimulator preferably includes a pulse generator for selectively generating antiarrhythmic pulses through the electrodes, and a sensor circuit connected to the same electrodes for sensing or detecting intrinsic (including induced) cardiac signals. The stimulator may also include arrhythmia induction circuitry.

DETAILED DESCRIPTION OF THE INVENTION

Figure 1B:
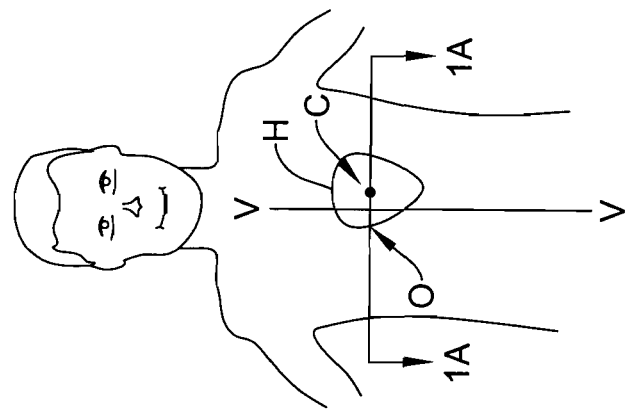
FIG. 1B shows a partial elevational view of a standing patient.
Figure 1A:
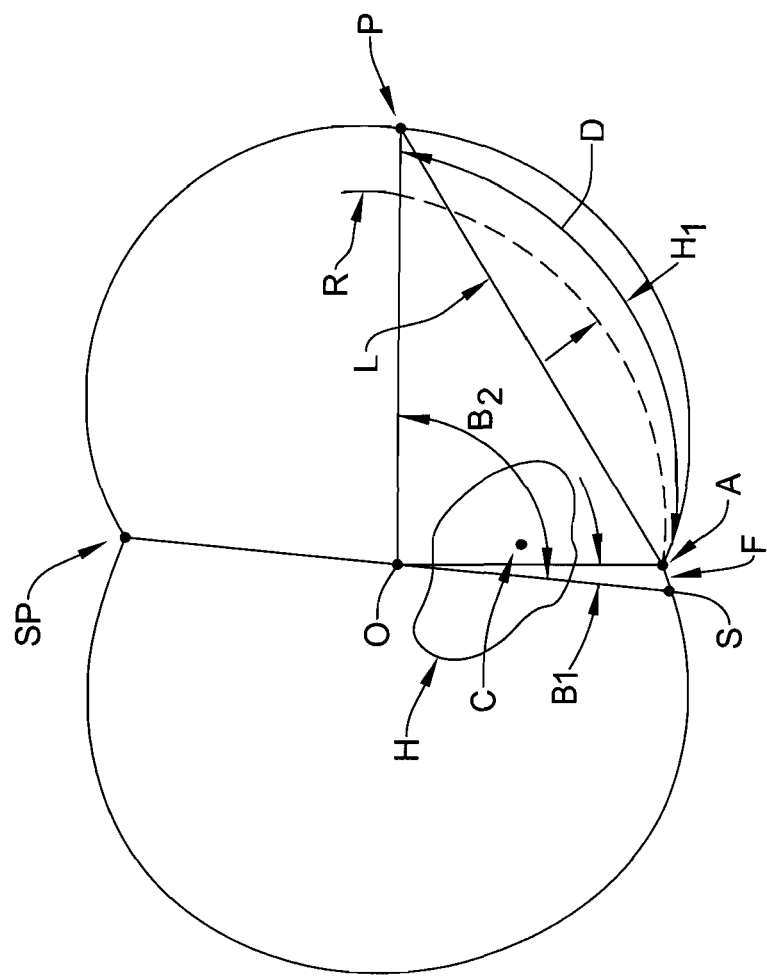
FIG. 1A shows a diagrammatic cross-sectional view of a patient taken through the center of the heart showing the positions of two subcutaneous electrodes and some references used to identify the same.

The present invention pertains to a novel device and method for applying stimulation to the heart of a patient. Before the device is described, several terms are first defined. FIG. 1A shows a cross sectional view and FIG. 1B is an elevational view of a standing patient. The heart of the patient is indicated at H as having a center of mass C. FIG. 1A also shows the sternum S and the spine SP. An imaginary line joins points S and SP, having a midpoint O. The vertical axis V-V through point O is defined as the central axis of the patient.

The present application is concerned with the optimal locations of two subcutaneous electrodes A (for anterior) and P (for posterior). These electrodes are implanted between the skin and the rib cage. As seen in FIG. 1A, electrode A is located as close to the sternum as possible. Its position is defined by the angle B1 between lines OS and OA. Similarly, the position of electrode P is defined by the angle B2 between the lines OS and OP. As will be described in more detail below, the electrodes are not point sources but rather are formed with substantially flat surfaces contacting the patient's tissues. In FIGS. 1A and 1B the points A and P represent the geometric centers of these contact surfaces.

As discussed above, historically, cardiac stimulation was applied through implanted electrodes positioned either within a cardiac chamber or in contact with the external cardiac tissue (or endocardium), or through external electrodes that are applied to the patient's skin. As disclosed in the co-pending applications listed above, it has been discovered that the heart can be stimulated very effectively with two electrodes disposed subcutaneously, that is, through two electrodes disposed between the skin and the rib cage. The two electrodes are connected to an implantable pulse generator arranged to generate pulses in a predetermined sequence, the pulse generator including a power supply, typically a battery, and a capacitor charged from the battery. It has been found that several parameters are important to the effectiveness of the device. These factors include the orientation and direction of the current flow through the heart (also referred to as 'the vector'), system impedance, electrode shape and structure, electrode placement and capacitor size. These parameters are interrelated to each other and hence the subject device is designed to insure that each of these parameters meets certain characteristics without compromising, or at least minimally compromising the characteristics of any of the other parameters.

The first and certainly one of the most important parameters is the vector characterizing the current flow. Optimally, the current flow should be uniform through the heart. Early internal defibrillators made use of mesh electrodes that were sewn to the heart, usually adjacent to the ventricles. This arrangement resulted in a relatively uniform vector. However, it required the patient to undergo a thoracotomy. More modern defibrillators rely on transvenous electrodes that generate highly localized vectors that are far from optimal, often giving rise to the need for using biphasic defibrillation shocks.

Figure 2A:
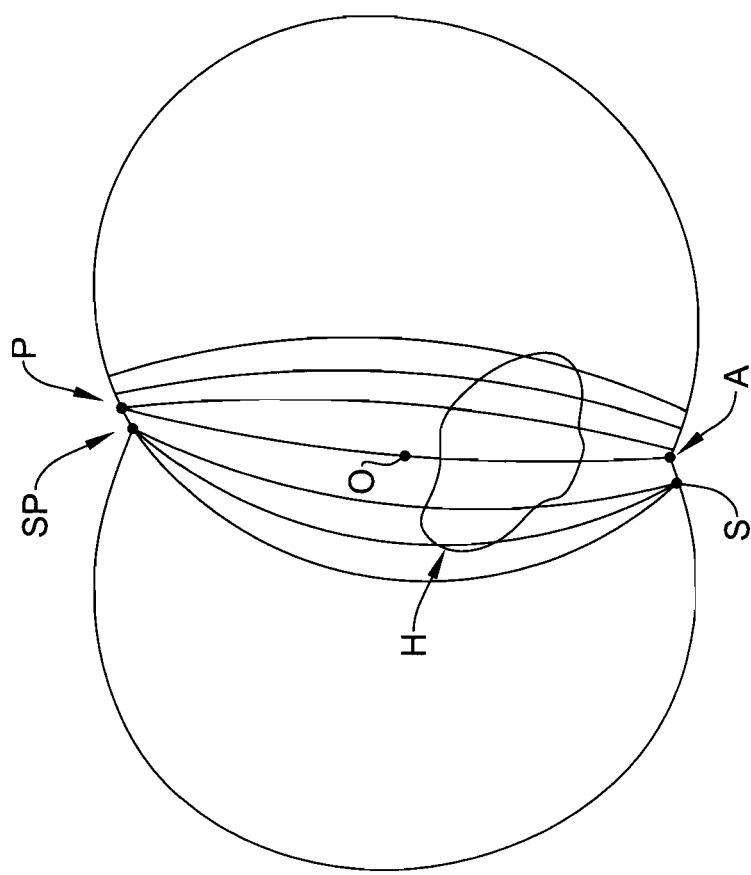
FIG. 2A shows a diagrammatic view of an electric field generated with one electrode disposed at the sternum and a second electrode located at an opposed position near the spine.
Figure 2B:
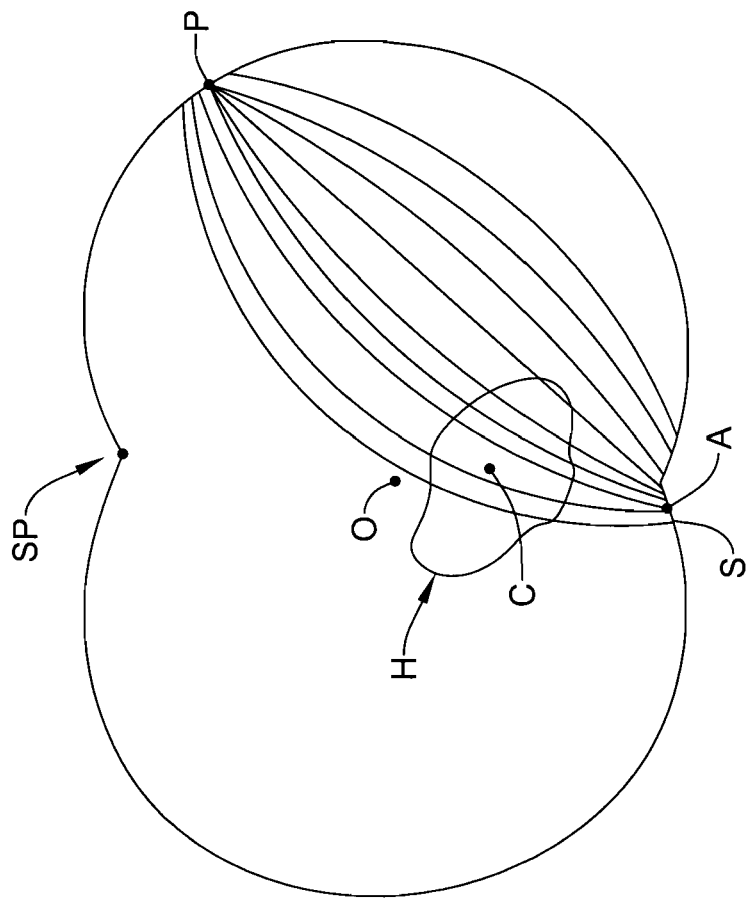
FIG. 2B shows a diagrammatic cross sectional view of the electric field generated by one electrode disposed at the sternum and a second electrode disposed in a posterior position behind the left arm.
Figure 2C:
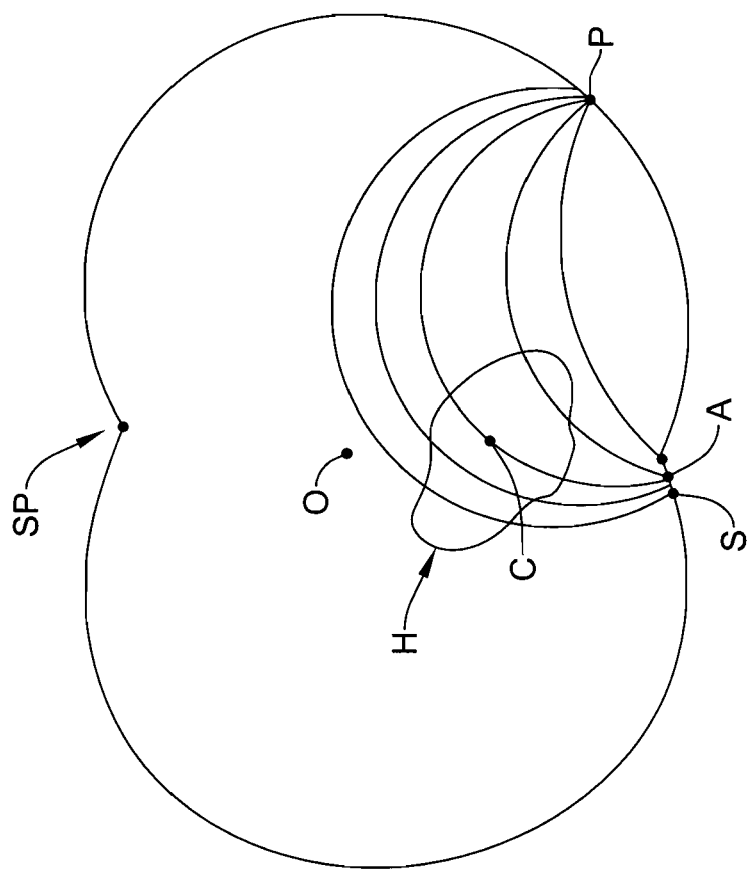
FIG. 2C shows a diagrammatic cross sectional view of the electric field generated by one electrode disposed at the sternum and the second electrode disposed in front of the left arm.

FIGS. 2A-2C show electric fields represented by electric field lines extending between electrodes A and P. In the present invention, in which subcutaneous electrodes are used, the obvious choice would be to place the electrodes in a diametrically opposed relation. For example, the A electrode could be placed at, or near the sternum, and the P electrode could be placed near the spine. FIG. 2A shows such a configuration. As shown in FIG. 2A, this configuration does indeed result in a fairly uniform vector propagating through the whole heart H. However, because the distance from the heart to the electrode P is fairly large as compared to the overall distance between the electrodes A and P, much of the energy of the vector is dissipated externally of the heart tissue and, in effect, is wasted. Therefore, the field intensity between the sternum S and the spine SP has to be fairly large if a sufficient field intensity is to be achieved within the heart. Studies have shown that this field intensity should be about 3-8 volts/cm across the cardiac tissues, using a bi-phasic waveform. This posterior position near the spine SP also has the disadvantage of being surgically challenging to access from an anterior or anterolateral incision.

Placing the electrode P at other positions along the patient's back does not solve the problem because, as the electrode P is moved to the left with respect to the spine, the distance between the electrodes increases and the electric field is shifted laterally so that one portion of the heart receives much less stimulation then the other, as shown in FIG. 2B. In addition, the amount of lung tissue between the two electrodes in creases as the electrode shifts posterolaterally, increasing the resistance and therefore decreasing field intensity.

However, as the electrode P is moved more toward the front past the armpit to the position indicated in FIG. 2C, the distance between the electrodes gets shorter and the vector is more uniform over a substantial portion of the heart as compared to the position in FIG. 2B.

It should be understood that the vectors shown in FIGS. 2A-2C represent three dimensional fields that extend above and below the horizontal plane defined by the center of heart C and the geometric centers of the electrodes.

Figure 3:
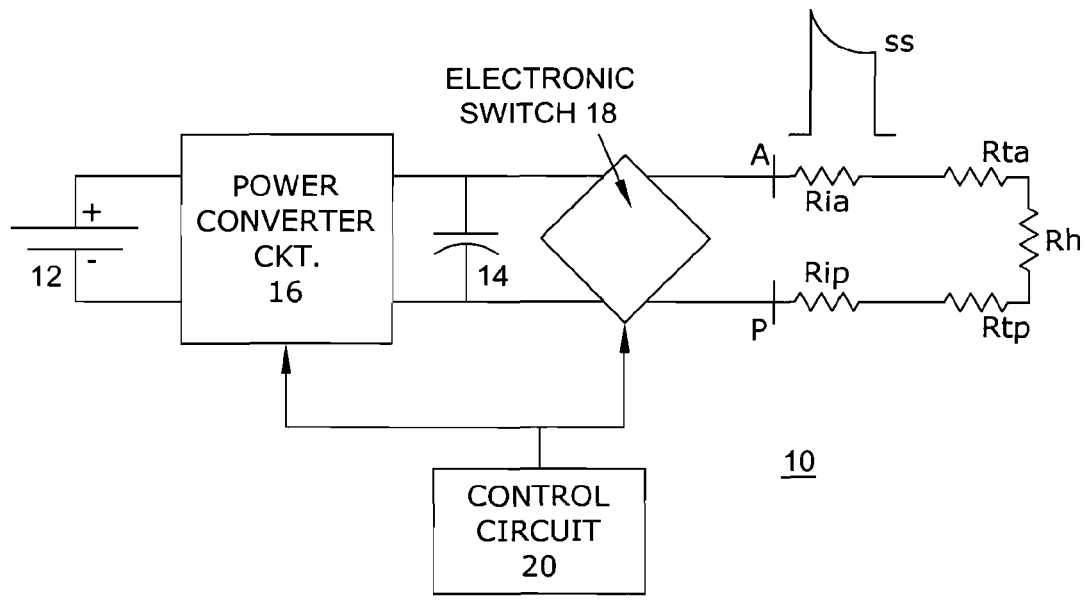
FIG. 3 shows a circuit diagram of a device constructed in accordance with this invention.

FIG. 3 shows a simplified block diagram of a device 10 constructed in accordance with this invention and is implantable as discussed in more detail below. The device 10 generally includes a battery 12 that is used to charge a capacitor 14 to a predetermined voltage (normally much higher than the battery voltage) by a power converter circuit 16. The energy stored in the capacitor 14 is selectively discharged through the electrodes A and P and the patient's tissues by using an electronic switch 18. The electronic switch normally consists of one or more switching elements (not shown) which may be arranged to form a bridge to provide the energy from the capacitor in monophasic, biphasic or multiphasic pulses. The converter circuit 16 and the electronic switch 18 are operated by a control circuit 20 which includes a microprocessor (not shown) that is programmed in the usual manner in accordance with the physical characteristics and cardiac condition of the patient. It should be understood that the FIG. 3 show a single battery 12 and a single capacitor 14, multiple batteries and/or capacitors may be provided as well.

As illustrated in FIG. 3, the active impedance seen by the device 10 may be represented as five resistors in series. Resistors Ria and Rip represent the resistances at the tissue/electrode interfaces at electrodes A and P, respectively. Rta and Rtp represent the resistance of the tissues between electrodes A and P and the heart H, respectively. Rh is the resistance of the heart. As current flows between the electrodes A and P, energy is dissipated in resistors Ria, Rta, Rtp and Rip. Thus, in order to save energy and therefore to minimize the size of the battery 12 and capacitor 14, the resistances should be as low as possible. Minimizing the resistance of the tissue resistors Rta and Rtp is difficult. The only selections that can be made that affects these parameters are the lengths of the current paths to and from the heart through the various bones, muscles, blood vessels and so on. In other words, the magnitudes of these resistors are minimized by positioning the electrodes as close as possible to the heart H.

Other factors that need to be considered in the design of the device are the size, shape and structure of the electrodes. These factors are important for two reasons: they affect the resistance of resistors Ria and Rip and they also affect the shape of the vector. It is well known that the resistance at the interface between two dissimilar materials (in this case the patient tissues and the electrode surface) is inversely proportional to the area of the interface. As the electrode surface area increases, the resistance goes down. However, if the electrodes are shaped with a large contact surface, they become too difficult to implant. Moreover, if the electrodes are two large, they will shunt the electric field around the ribs, and away from the heart.

Optionally, the effective contact area of the electrode(s) may be augmented or increased without changing the dimensions of the electrode(s) thereby mitigating the electrode-tissue interface resistance problem without complicating the implantation process. Means for increasing the effective area of the electrode(s) include using fractal, or other microscopic surface treatment, or by using convoluted or corrugated surfaces.

The electrode interface resistors Ria and Rip are in series with the tissue resistors Rta and Rtp. When the combined resistance of the electrode interface resistors is much larger than the combined resistance of the tissue resistors and the resistance of the heart (i.e., Ria+Rip>Rta+Rtp+Rh), the magnitude of the current between the electrodes (and, consequently, the magnitude of the electric field) is essentially dependent on the combined resistance of the electrode interface resistors, i.e., the electrode interface resistors are dominant. Conversely, if the combined resistance of the tissue resistors is much greater than the combined resistance of the electrode interface resistors then the current magnitude is substantially independent of the electrode interface resistors, i.e., the tissue resistors are dominant.

We have found that the electrode interface resistors are dominant if the electrodes have a surface area of up 10 cm$^2$ per electrode. Above 15 cm$^2$/electrode, the tissue resistors become dominant and the electrode interface resistors have very little effect.

A further factor to be considered in determining the inner surface area of the electrodes is the distance from the electrodes to the heart. We have found that the anterior electrode, which is closer to the heart, should not exceed the inner surface area of the posterior electrode. Preferably, the inner surface area of the anterior electrode should be smaller than the inner surface area of the posterior electrodes. For example, the inner surface area of the anterior electrode could be 5-15 cm$^2$ and the inner surface area of the posterior electrode could be 15-40 cm$^2$.

Figure 4A:
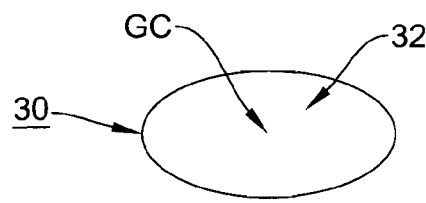
FIG. 4A shows a side elevational view of an electrode used in the device of FIG. 3.
Figure 4B:
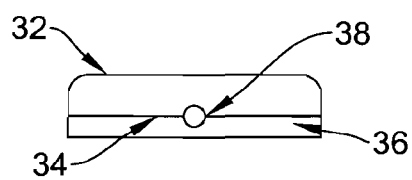
FIG. 4B shows a bottom view of the electrode of FIG. 4A.

As mentioned above, the shape, size and edges of the electrodes all affect the shape of the vector. It is well known that a sharp edge on a conductor tends to focus and concentrate the electric field. Therefore, preferably the electrodes A and P are made without any sharp edges. FIGS. 4A and 4B illustrate such an electrode 30. The electrode is shown as having an oval shape, but it can have other configurations as well. For example, the electrode may be made with a curved rather than a linear profile. As seen in the Figures, the electrode is shaped so that all of its edges are curved. It has an inner surface 32 with a geometric center GC and an outer surface 34. Preferably, the electrode 30 is made of a material having a low resistivity and is biologically inert. For example, the electrode 30 can be made of stainless steel, titanium, titanium iridium, titanium oxides, platinum and other alloys.

In the embodiment of FIGS. 4A and 4B, the outer surface 34 of the electrode 32 is covered with a layer 36 made of an electrically insulating material. The electrode is connected to a wire 38 that is used to couple the electrode to the circuitry shown in FIG. 3.

Figure 4C:
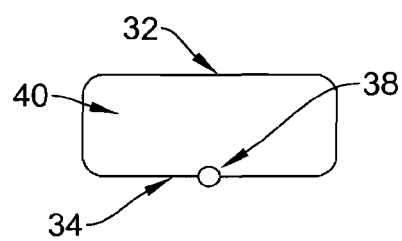
FIG. 4C shows a bottom view of an alternate embodiment of the electrode of FIG. 4A.

The electrode of FIGS. 4A and 4B can be implanted as either electrode A or P with its inner surface 32 being disposed vertically, and facing generally inward, toward the heart H. The insulating layer 36 is provided to insure that the electric field between the two electrodes is restricted toward the heart. In an alternate embodiment shown in FIG. 4C, the electrode 40 is made without an insulating layer 36 on surface 34, thereby generating a broader, more dispersed and less preferred electric field, and reducing the effective resistance of the respective electrode interface resistor. Of course, the electrode edges and corners are still rounded, as shown.

As seen in FIG. 3, the device 10 includes a capacitor 14 which is charged up to a nominal voltage by a power converter circuit 16 using energy from the battery 12. This is a standard arrangement common to most other ICDs. Typically, the impedance between the electrodes of a conventional ICD is about 50 ohms. When a capacitor charged to a nominal voltage is coupled by an appropriate switching means to the electrodes, a stimulation signal is generated that decays exponentially with a time constant determined by the impedance between the electrodes and the value of the capacitor. Normally, this signal is cut off before it decays completely, as shown in FIG. 3 as SS. Pulse SS is usually characterized as a truncated exponential signal. As discussed above, often biphasic stimulation signals are used. A biphasic stimulation signal includes the signal SS followed immediately by a second truncated exponential of opposite polarity.

For conventional ICDs it was found that the truncated signal SS was most effective when its time constant was about 5 msec, which matches the natural chronaxie of the body. That means that the capacitor has to have a value of about 100 microfarads.

In the present device the total system impedance shown in FIG. 3 can be optimized to a value of about 70-75 ohms, depending on the various parameters discussed above. The corresponding value for capacitor 14 in order to obtain the same time constant is about 70 microfarads. It has been confirmed that this time constant is also most effective for the present subcutaneous device. More particularly, it was found that lower stimulation threshold levels could be used with this time constant.

Returning to FIGS. 2A-C, in addition to the shape, size and contact area of the electrodes, the positions of the electrodes A and P will have some effect on the vector. It has been found that ideally the vector through the heart should have an average gradient of about 3-8 volts/cm. The peak voltage between the electrodes required to generate this vector varies from patient to patient in accordance to his or her size, as well as the placement of the electrodes.

Figure 5:
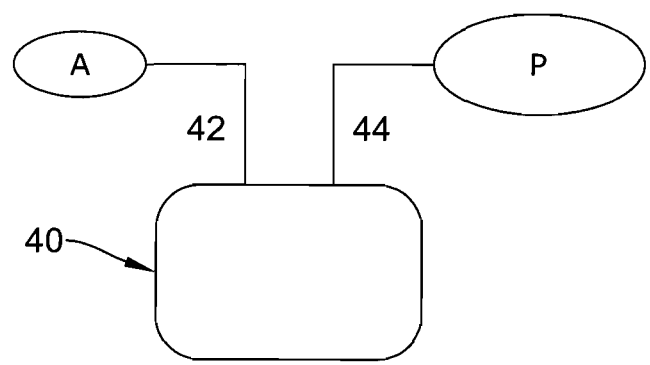
FIG. 5 shows a block diagram of a first embodiment of the device, wherein the device has three elements.

In one embodiment of the invention shown in FIG. 5, the device 10 has three elements: two electrodes A and P and a cardiac stimulator disposed in a housing 40 incorporating all the other elements shown in FIG. 3 and cooperating to deliver stimulating pulses to the heart through the electrodes. The electrodes A, P are connected to the housing 40 by leads 42, 44. For this embodiment, the electrodes are implanted subcutaneously so that their respective electrode centers (corresponding to the geometric center GC of each inner surface 32 in FIG. 4A) are disposed at the positions shown in FIG. 2C. Preferably, the electrode P is positioned so that the angle B1 as defined in FIG. 1A is about 5-30 degrees and angle B2 is about 60-120 degrees.

Alternatively, the relative positions of electrodes A and P may be determined as a circumferential distance D. Referring again to FIG. 1A, broken line R shows the outer surface of the patient's rib. The distance D is measured between the electrodes A and P along an imaginary line extending parallel to the rib line R and radially displaced therefrom by a distance H1. The electrode A is then placed at a distance F from the sternum along the same imaginary line. Some preferred values for distances are as follows: D is in the range of 15-35 cm; H1 is in the range of 0-3 cm; and F is in the range of 2-10 cm.

The relative positions of electrodes A and P may also be defined as a chord length L, wherein L is the length of the straight line extending between A and P as shown. Typically L is in the range of 15-25 cm.

Figure 6:
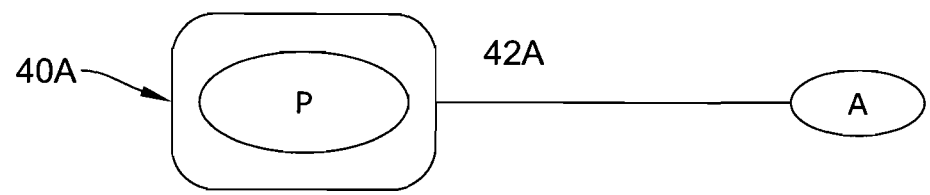
FIG. 6 shows a block diagram of a second embodiment of the device, wherein the device has two elements.
Figure 7:
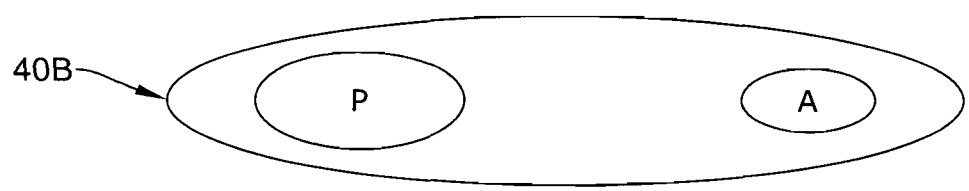
FIG. 7 shows a block diagram of a third embodiment of the device, wherein the device has one element.

In the embodiment shown in FIG. 5, the housing 40 is separate from the electrode and is implanted at the same time as the electrodes at any suitable site in the body. In another embodiment of the invention shown in FIG. 6, the housing 40A is an active housing in the sense that one of the electrodes, for instance, electrode P is formed on the housing as shown. The other electrode, in this case A, is coupled to the housing 40A by a lead 42A. In this case the housing 40A with the electrode P integral therewith is implanted so that the electrode P is in the position shown in FIG. 1, while the free electrode A is in the position adjacent to the sternum, as explained above. Alternatively, the P electrode may be the free electrode and the electrode A may be formed on the housing 42A. In this latter configuration, the housing 42A is positioned near the sternum.

A third embodiment is shown in FIGS. 7, 8A, 8B and 8C. In this embodiment, the device is a unitary device in the sense that neither electrode is physically separated from the housing holding the pulse generator. Instead, the device consists of a unitary housing 40B which has an elongated body with the electrodes A and P being formed on the housing as shown.

This arrangement has several advantages. First, it eliminates the need for any leads. This is an important advantage for safety and reliability.

Figure 8A:
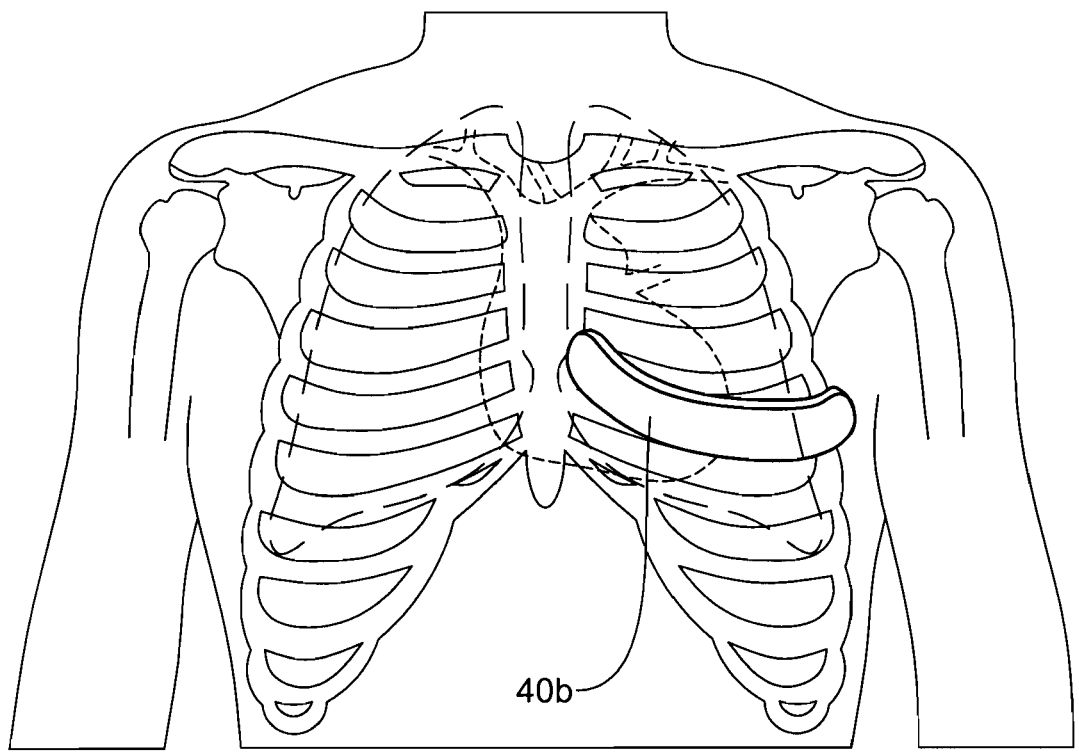
FIG. 8A shows a three dimensional front rendering of a patient's rib cage with the device of FIG. 7 in place.
Figure 8B:
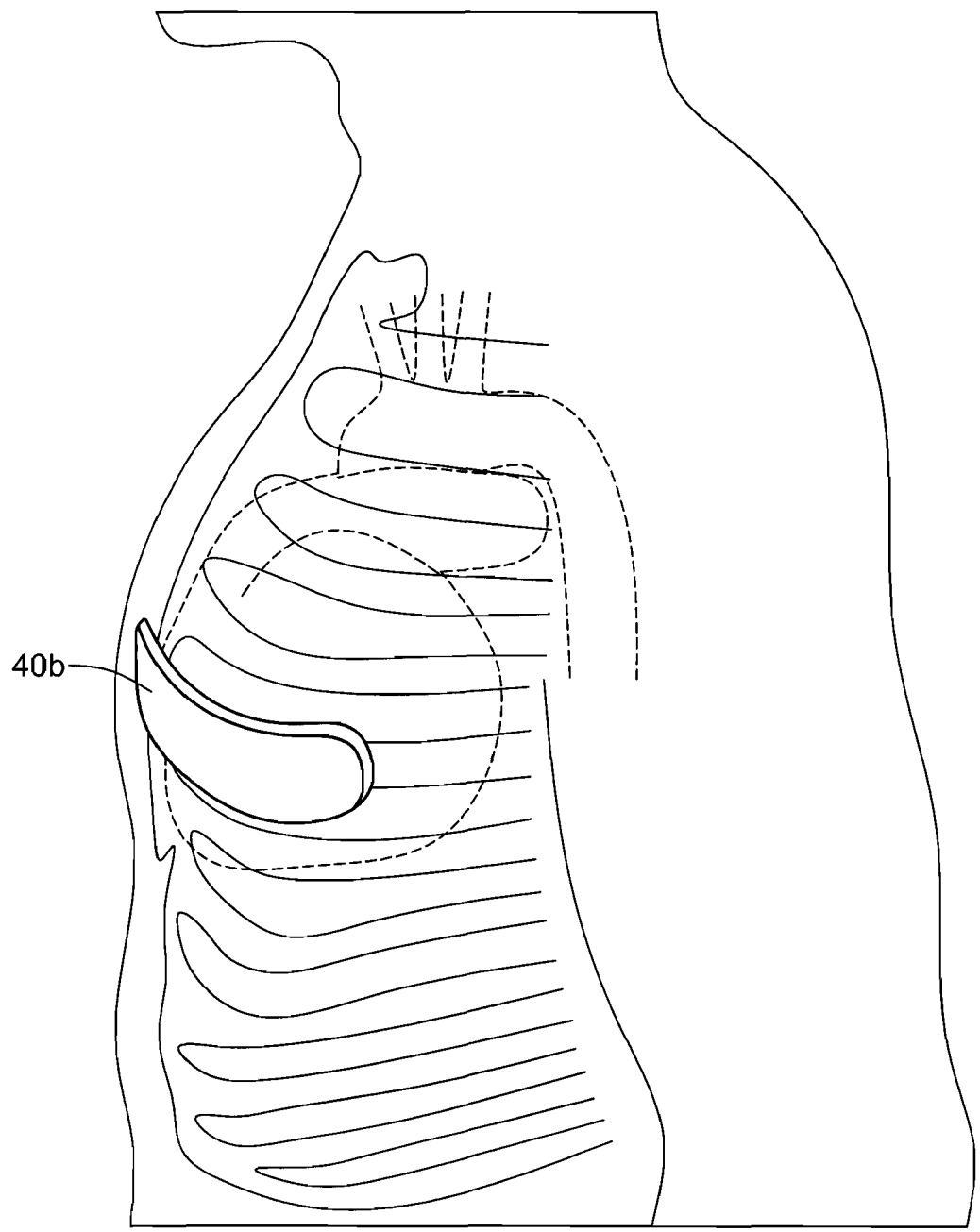
FIG. 8B shows a three dimensional left rendering of the patient's rib cage of FIG. 8A.
Figure 8C:
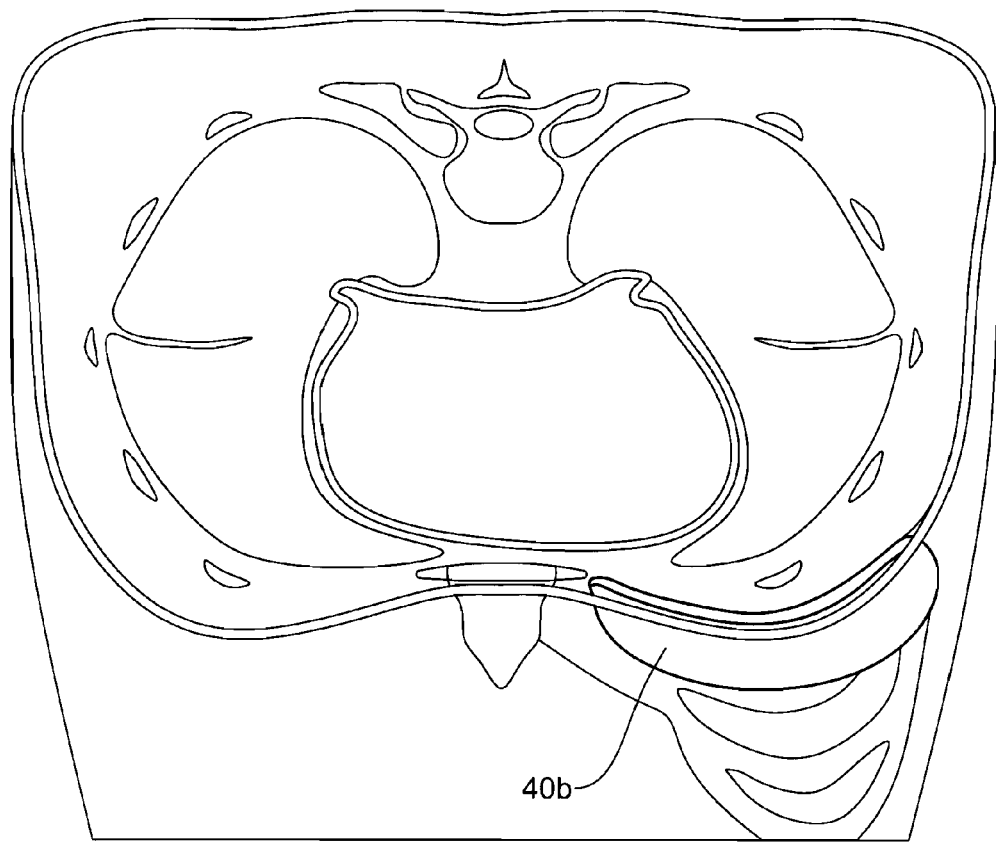
FIG. 8C shows a cross-sectional top three dimensional rendering of the rib cage of FIG. 8A.

Another advantage is that it is much easier and faster to implant. FIGS. 8A, 8B and 8C show somewhat diagrammatic but anatomically correct renderings of the chest cavity of a patient with the unitary housing 40B implanted just outside the rib cage between the fifth and sixth ribs. In order to insure that it fits into this location properly, the unitary housing has curved surfaces which conform in both shape and size to the curvature of the patient's rib cage. As a result, the unitary housing 40B is easy to implant, and, since it creates only a slight protrusion of the skin, it is cosmetically more acceptable as well. The unitary housing 40B can be implanted through a single vertical incision (not shown) which need not be greater than the width of the housing. The housing is then inserted in one direction through the incision until it is disposed wholly under the skin. The unitary housing 40B is then slipped back under the skin, past the incision to the position shown in the Figures.

Figure 8D:
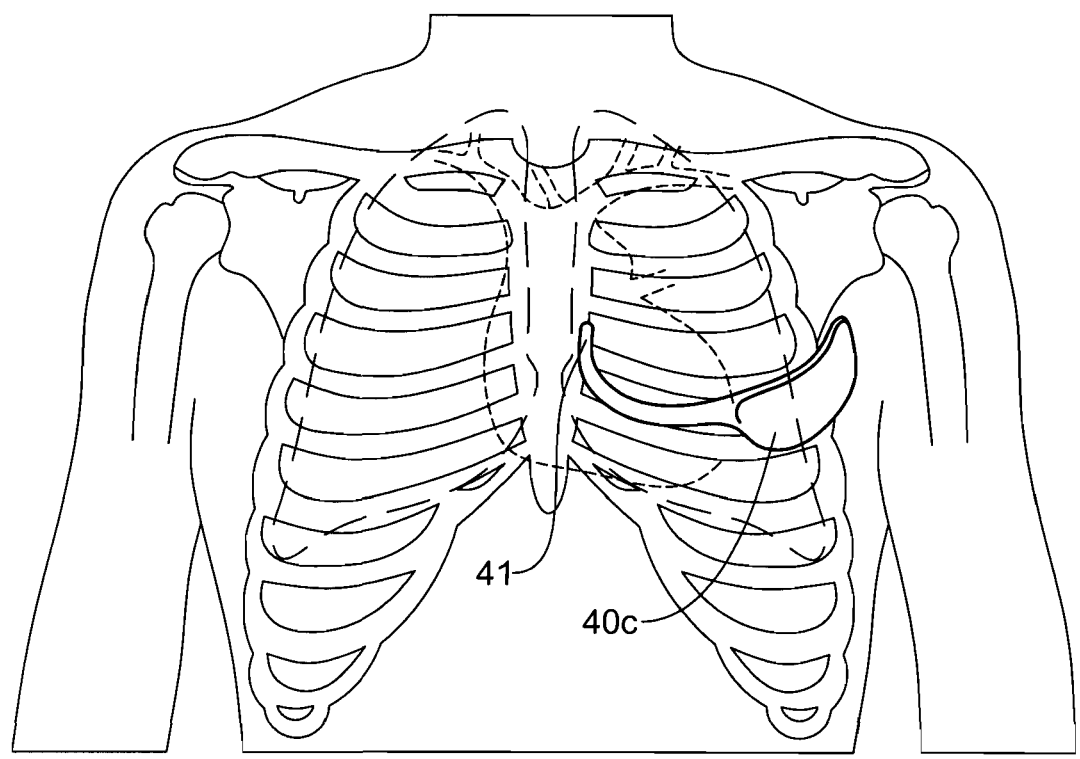
FIG. 8D shows a three dimensional front rendering similar to FIG. 8A with slightly different version of the subcutaneous device.
Figure 8E:
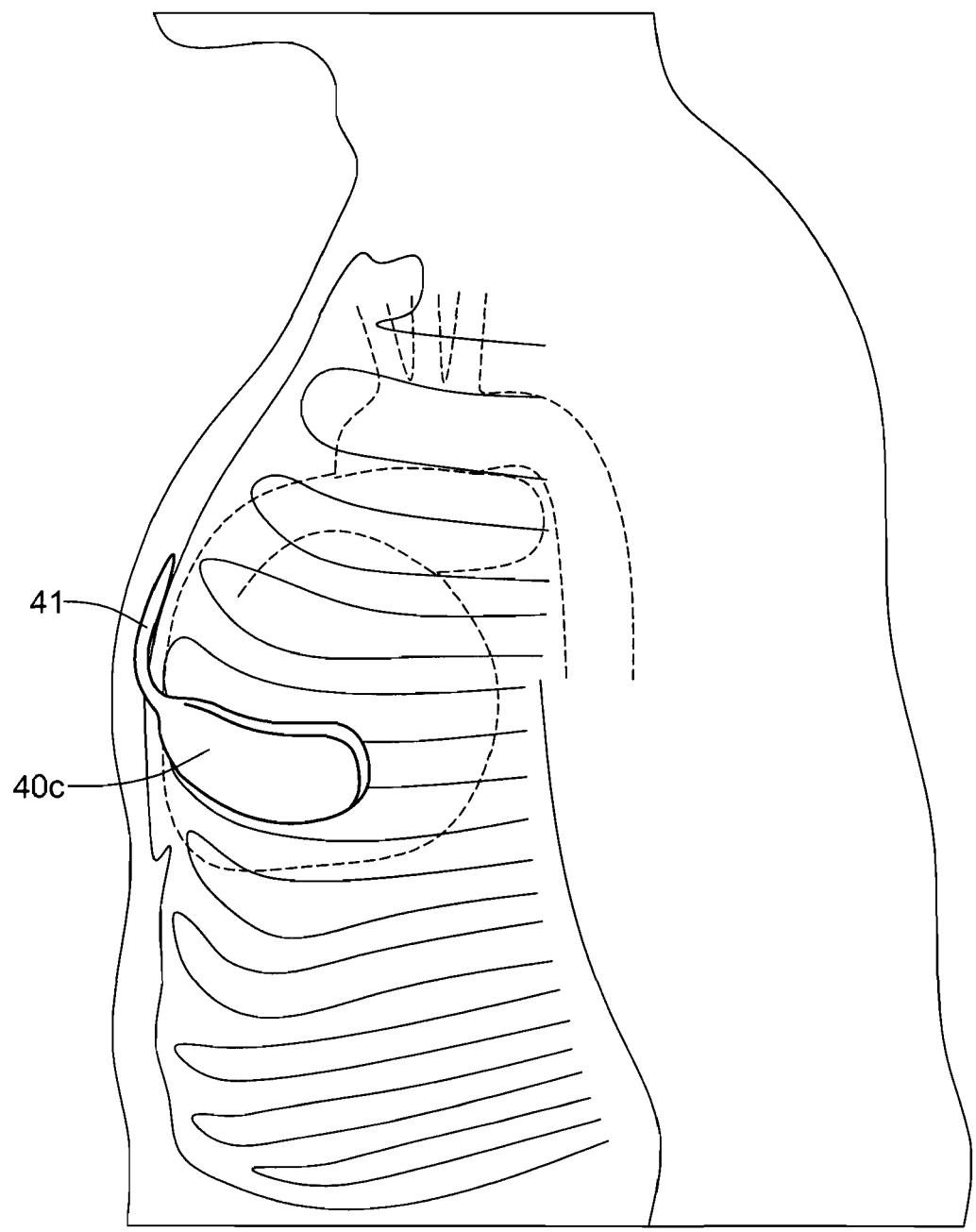
FIG. 8E shows a left rendering of the device of FIG. 8D.

FIGS. 8D and 8E shows a different embodiment of the invention. In this embodiment, unitary housing 40C has a somewhat flexible extension 41C. As can be seen in the Figures, the housing 40C is implanted so that its extension 41C curves upward adjacent to the sternum so that it becomes almost vertical.

As best seen in FIGS. 8A and 8D, the ribs are not perpendicular to the sternum but join the sternum at an angle. In order for the housing 40B and 40C to conform to the space between the ribs, it must be implanted at this angle as well. Based on the considerations discussed above in conjunction with FIGS. 1 and 2C, the electrodes must be positioned and shaped so that they generate a vector along a plane that passes through the center of gravity C of the heart and the geometric centers GC of the electrodes A and P and is slanted to follow the angle of the ribs as well.

In this latter embodiment, since the surfaces of the unitary housing are non-planar, the electrodes A and P are non-planar as well. The positions of their geometric centers are defined by the angles B1 and B2.

Figure 9:
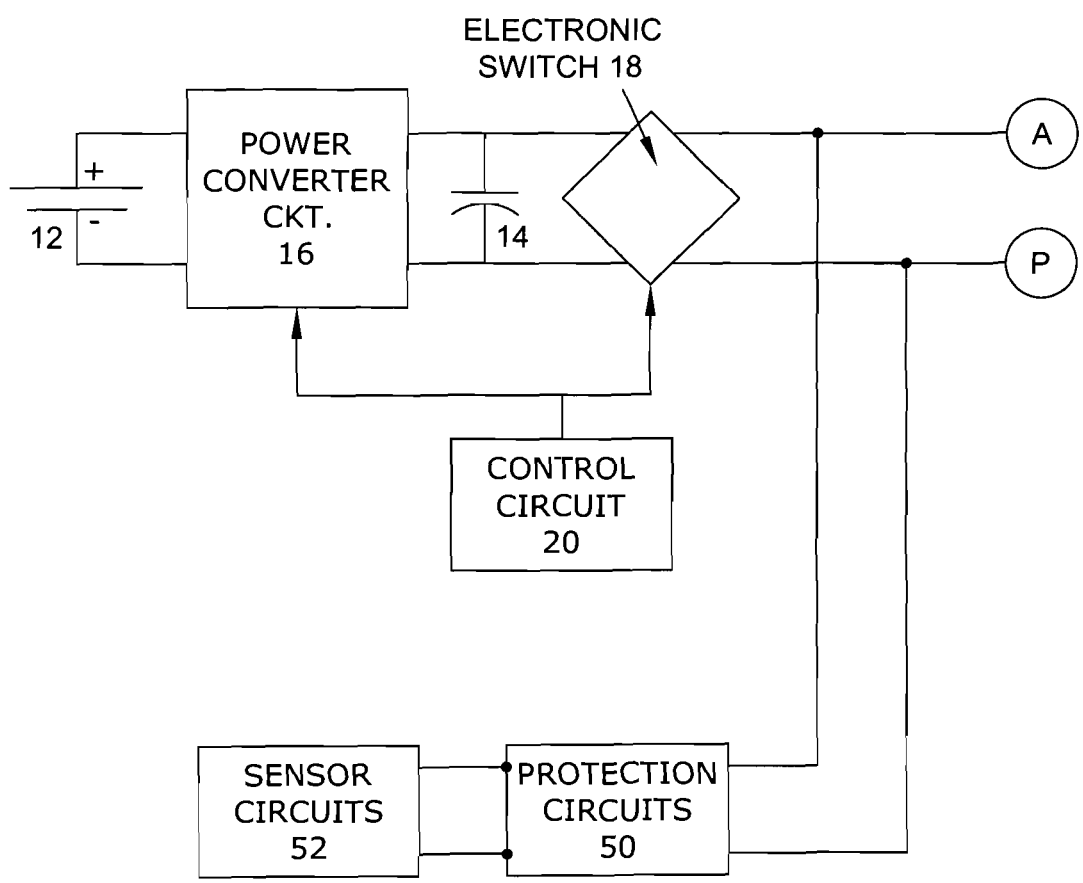
FIG. 9 shows a circuit diagram of the device also showing the sensor circuits.

The devices shown in the Figures operate in a similar manner to conventional ICDs, and as such, have the capability of sensing intrinsic cardiac activities, and to induce arrhythmia as well. FIG. 9 shows a circuit diagram similar to the one in FIG. 3 but has been modified to show the sensing function. As can be seen in this Figure, the electrodes A and P are also connected to protection circuits 50, and then to sensing circuits 52. The purpose of the protection circuits is to insure that the sensing circuits are not subjected to the high voltages generated across the electrodes A and P while the shocks are applied. As mentioned above, arrhythmia induction circuitry may also be incorporated into the device.

Numerous modifications may be made to this invention without departing from its scope as defined in the appended claims.

We claim:

1. A method of implanting an implantable cardiac device for subcutaneous implantation in a patient, the patient having a torso including a ribcage, sternum and spine, the method comprising:
   implanting a first electrode, electrode A, having a surface area in the range of about 5-15 cm$^2$ at an anterior position adjacent to the sternum of the patient; and
   implanting a second electrode, electrode P, at a second position on the ribcage of the patient in front of the armpit of the patient;
   wherein electrode A and electrode P each has an inner metallic surface;
   wherein electrode A and electrode P are coupled to defibrillation circuitry for delivering a defibrillation shock between electrode A and electrode P.

2. The method of claim 1 wherein the surface area of electrode A is less than the surface area of electrode P.

3. The method of claim 1 wherein the circuitry for delivering a defibrillation shock comprises a capacitor having a capacitance in the range of about 70 microfarads.

4. The method of claim 1 wherein the chord length between electrode A and electrode P, once implanted, is in the range of 15-25 cm.

5. The method of claim 1 further comprising implanting a housing containing the defibrillation circuitry, such that electrode A is on a first lead coupled to the housing and electrode P is on a second lead coupled to the housing.

6. The method of claim 1 wherein electrode P is located on a housing which contains the defibrillation circuitry, and electrode A is coupled to the housing with a lead.

7. The method of claim 1 wherein electrode A and electrode P are located on opposing ends of a housing which contains the defibrillation circuitry.

8. The method of claim 1 wherein electrode P has a surface area in the range of 15-40 cm$^2$.

9. The method of claim 8 wherein the surface area of electrode A is less than the surface area of electrode P.

10. The method of claim 8 wherein the circuitry for delivering a defibrillation shock comprises a capacitor having a capacitance in the range of about 70 microfarads.

11. The method of claim 8 wherein the chord length between electrode A and electrode P, once implanted, is in the range of 15-25 cm.

12. The method of claim 8 further comprising implanting a housing containing the defibrillation circuitry, such that electrode A is on a first lead coupled to the housing and electrode P is on a second lead coupled to the housing.

13. The method of claim 8 wherein electrode P is located on a housing which contains the defibrillation circuitry, and electrode A is coupled to the housing with a lead.

14. The method of claim 8 wherein electrode A and electrode P are located on opposing ends of a housing which contains the defibrillation circuitry.

15. The method of claim 8 wherein electrode A and electrode P each have an oval shape.

16. The method of claim 1 wherein electrode A and electrode P each have an oval shape.

\* \* \* \* \*